(12) United States Patent
Dini et al.

(10) Patent No.: US 11,058,138 B2
(45) Date of Patent: Jul. 13, 2021

(54) COMPOSITION FOR CALCIUM SUPPLEMENTATION

(71) Applicant: ABIOGEN PHARMA S.P.A., Pisa (IT)

(72) Inventors: Laura Dini, Pisa (IT); Fabio Neggiani, Pisa (IT); Samuele Zanatta, Santandra' di Povegliano (IT)

(73) Assignee: ABIOGEN PHARMA S.P.A., Loc. Ospedaletto (IT)

( * ) Notice: Subject to any disclaimer, the term of this patent is extended or adjusted under 35 U.S.C. 154(b) by 0 days.

(21) Appl. No.: 16/644,286

(22) PCT Filed: Sep. 6, 2018

(86) PCT No.: PCT/EP2018/073979
§ 371 (c)(1),
(2) Date: Mar. 4, 2020

(87) PCT Pub. No.: WO2019/048532
PCT Pub. Date: Mar. 14, 2019

(65) Prior Publication Data
US 2020/0375238 A1    Dec. 3, 2020

(30) Foreign Application Priority Data

Sep. 6, 2017  (IT) .................. 102017000099690

(51) Int. Cl.
| | | |
|---|---|---|
| *A23L 33/16* | (2016.01) | |
| *A23L 29/269* | (2016.01) | |
| *A23L 27/30* | (2016.01) | |
| *A23L 29/00* | (2016.01) | |
| *A23L 33/00* | (2016.01) | |
| *A61K 9/14* | (2006.01) | |
| *A61K 33/06* | (2006.01) | |
| *A61K 47/12* | (2006.01) | |
| *A61K 47/26* | (2006.01) | |
| *A61K 47/36* | (2006.01) | |
| *B65D 75/48* | (2006.01) | |

(52) U.S. Cl.
CPC .............. *A23L 33/16* (2016.08); *A23L 27/37* (2016.08); *A23L 29/035* (2016.08); *A23L 29/27* (2016.08); *A23L 33/40* (2016.08); *A61K 9/14* (2013.01); *A61K 33/06* (2013.01); *A61K 47/12* (2013.01); *A61K 47/26* (2013.01); *A61K 47/36* (2013.01); *B65D 75/48* (2013.01); *A23V 2002/00* (2013.01)

(58) Field of Classification Search
CPC ........ B65D 75/48; A61K 47/36; A61K 47/26; A61K 47/12; A61K 33/06; A61K 9/14; A23L 33/40; A23L 29/035; A23L 27/37; A23L 29/27; A23L 33/16; A23V 2002/00
See application file for complete search history.

(56) References Cited

U.S. PATENT DOCUMENTS

| | | | |
|---|---|---|---|
| 4,851,221 A | 7/1989 | Pak et al. | |
| 5,075,499 A | 12/1991 | Walsdorf et al. | |
| 5,232,709 A | 8/1993 | Saltman et al. | |
| 5,759,575 A | 6/1998 | Gergely et al. | |
| 5,817,351 A * | 10/1998 | DeWille ................ | A61K 33/06 426/74 |
| 9,439,853 B2 | 9/2016 | Julien et al. | |
| 2005/0181096 A1* | 8/2005 | Zeller ................ | A23L 2/39 426/74 |
| 2007/0065542 A1 | 3/2007 | Pak | |
| 2007/0196539 A1 | 8/2007 | Yang et al. | |
| 2009/0155432 A1* | 6/2009 | Walter ............. | A21D 13/24 426/302 |
| 2012/0280055 A1* | 11/2012 | Schneidmiller ....... | A01M 29/12 239/6 |
| 2015/0239897 A1* | 8/2015 | Chen ................ | C07D 487/04 514/265.1 |
| 2016/0367558 A1* | 12/2016 | Oppenheimer .......... | A61P 9/00 |
| 2020/0339532 A1* | 10/2020 | Gurney .............. | C07D 401/06 |

OTHER PUBLICATIONS

Search Report and Written Opinion of PCT/EP2018/073979 dated Nov. 22, 2018.

* cited by examiner

*Primary Examiner* — Blessing M Fubara
(74) *Attorney, Agent, or Firm* — Silvia Salvadori, P.C.; Silvia Salvadori

(57) ABSTRACT

The present invention relates to a formulation in the form of an aqueous suspension comprising calcium citrate. Said formulation exhibits excellent stability and compliance and finds use in calcium supplementation in subjects in need of such supplementation.

33 Claims, No Drawings

COMPOSITION FOR CALCIUM SUPPLEMENTATION

This application is a U.S. national stage of PCT/EP2018/073979 filed on 6 Sep. 2018, which claims priority to and the benefit of Italian Patent Application No. 102017000099690, filed on 6 Sep. 2017, the contents of which are incorporated herein by reference in their entireties.

FIELD OF THE INVENTION

The invention concerns an aqueous suspension formulation comprising calcium citrate that may be used for calcium supplementation in subjects in need of the above supplementation.

The use of said composition prevents and counteracts the onset of diseases related to bone mass loss, such as osteoporosis and fractures.

STATE OF THE ART

Calcium is one of the most abundant minerals in the human organism, the major constituent of bones and teeth, and plays an important role in various physiological systems. Since our body does not produce minerals, its content is totally dependent on its external intake through diet or supplementation.

Its correct intake is therefore essential for the development of teeth in children, and for bone health throughout the entire life of a human being. The level of calcium in our body is, in fact, also one of the main factors involved in the development of osteoporosis in elderly subjects, who represent an increasingly large segment of the population, given the lengthening of the average population lifetime, especially in the more developed countries.

In 1994, for example, in the United States, the National Health Institute (NIH) Consensus Development Panel reviewed the recommended daily intake for calcium, which was established between 800 and 1500 mg per day, depending on age.

Over time, numerous formulations of calcium supplements and drugs have been developed to allow the correct supplementation to meet its requirements.

The most widespread products on the international market are products based on calcium carbonate, mainly in the form of a tablet, in various dosages, mainly of 500 and 1000 mg.

While these products obviously meet the need for calcium supplementation, on the other hand they are not exempt from side effects. As it is by now well known in the literature, in fact, prolonged intake of calcium carbonate is often associated with the onset of kidney stones (nephrolithiasis).

De facto, the many pharmaceutical development attempts carried out so far by companies operating in this sector, are aimed at the research of calcium salts alternative to calcium carbonate, that are readily absorbable in the digestive tract, more bioavailable, and therefore able to provide more effectively the desired calcium doses, while inhibiting calcium nephrolithiasis.

Various calcium salts have been considered over time (phosphate, citrate, chloride, acetate, lactate, gluconolactate, etc.), each of which provides a different amount of calcium, depending on its molecular weight, and has its own solubility, that during transit through the intestinal tract responsible for absorption determines the bioavailability thereof.

One of these, calcium chloride, for example, is a salt with high solubility that is currently used exclusively by intravenous injection route in the case of cardiopulmonary emergencies; its oral intake, as a calcium supplement, especially for long periods, would not be possible, because it would cause irritation of the mucous membranes of the entire digestive tract, would put patients at risk of acidosis in the blood and urine, and would require constant monitoring of levels of carbon dioxide and chlorine in patients.

Alternatively, the use of calcium phosphate, a salt which is also insoluble and with a calcium content of 40%, fully comparable to calcium carbonate, would not have any particular advantage, neither in formulation nor in clinical terms, with respect to carbonate, being inter alia not usable in subjects with achlorhydria, such as the elderly, who represent the population segment most in need of supplementation, for which the clinical efficacy of this salt seems to be even lower than that of carbonate. The potential use, instead, of calcium acetate, already known and used in clinical practice by virtue of its chelating properties towards phosphate ions, which make it the drug of choice in cases of severe renal insufficiency, would not be possible in the dosages required to allow a correct supplementation of calcium, as it would magnify the typical side effects of its chronic intake, such as abdominal pain, constipation, or diarrhea.

A further salt that has been particularly studied over the years, proving to be considered a valid alternative to calcium carbonate, is calcium citrate.

This salt in fact exhibits a high bioavailability, even about double the bioavailability of calcium phosphate, and about 20-30% higher than that of calcium carbonate. This greater bioavailability seems to be dependent on the different absorption mechanisms involved at the intestinal level: calcium is absorbed at the intestinal level by active transport when in the ionized form, and by passive diffusion through the paracellular pathway when calcium is in the form of a complex with the citrate ion.

It is also perfectly tolerated, and therefore usable in subjects with achlorhydria, it is thus suitable for the wide elderly patients segment, for subjects with inflammatory bowel disease, for subjects with absorption disorders, for subjects treated with H2-blockers or proton pump inhibitors, and it is associated with very reduced risks of development of kidney stones (nephrolithiasis), compared to calcium carbonate, being the citrate ions inhibitors of crystallization.

In addition, as it can be freely taken at any time of the day, both in the presence and in the absence of food, it gives the pharmaceutical product or integrator containing it a wide flexibility of use.

Therefore, calcium citrate seems to represent nowadays the most effective therapeutic alternative, and with fewer side effects compared to calcium carbonate, if one wants to prepare pharmaceutical products or supplements for calcium supplementation.

From a formulative point of view, the use of calcium citrate is, however, far from simple for various reasons.

Firstly, calcium citrate molecule contains only about 21% of calcium (compared to, for example, 40% in the molecule of calcium carbonate), therefore, during the preparation of pharmaceutical products or tablet supplements, in order to administer equal dosages of calcium, typically 500 or 1000 mg per unitary dose, it is necessary to achieve volumes and weights for the single doses proportionally much higher, which in fact make it impossible to prepare tablets having such dosages. Such tablets would, in fact, be more fragile, brittle, difficult to machine and therefore to be produced, and, in any case, should the technological problems related to their production be overcome, very large tablets, difficult to swallow by the patients, especially by the elderly and children, would be obtained.

The few formulations, based on calcium citrate alone, that reached the market have in fact much lower dosages than those recommended, typically around 200 mg of calcium per unitary dose, and involve poor compliance, requiring patients to take 3-5 daily tablets to reach the recommended daily dose.

Nevertheless, in the attempt to administer calcium in the form of calcium citrate, formulations in the form of solubilizable powders at the time of intake (for example, effervescent powders or tablets) by dissolution in certain volumes of water, typically not less than 150-200 ml per dose, have been studied and developed over time.

These preparations typically contain calcium carbonate or other calcium salts, also in mixture thereof, and citric acid, or citric acid in mixture with other organic acids, such as for example tartaric acid or malic acid, which favor calcium solubilization in the solution and therefore allow partial or total conversion into readily assimilable soluble citrate calcium.

In reality, this type of pharmaceutical preparations still have disadvantages, in terms of patient compliance, as they require the availability of water at the time of the intake, which patient does not always have with him, and which would in any case be forced to find; the need to ingest a volume of preparation not less than 150-200 ml, that is a fair amount of liquid that not all patients like to drink; as well as the fact that the calcium salt present in the preparation takes a few minutes to completely solubilize and, still, tends to reprecipitate easily.

These evidences and limits clearly impact on the easiness and pleasantness of the preparation intake for the patient, thus reducing compliance.

As an example, in the patent document U.S. Pat. No. 5,759,575, a wide review of the solution attempts investigated over time to solve the issues related to poor solubility of calcium salts, their tendency to reprecipitate, and the fact that the powders and effervescent tablets prepared are often difficult to machine, is reported.

The object of the present invention is therefore to provide a formulation comprising calcium citrate which does not give rise to the aforementioned disadvantages.

In particular, the object of the present invention is to provide a formulation comprising calcium citrate which can be easily taken in any situation, without the need to find a solution in which to perform its dissolution.

The object of the present invention is therefore to provide a formulation comprising calcium citrate which can be ready-to-use, easy to take by both elderly and pediatric patients.

Therefore, the ultimate object of the present invention is to provide a ready-to-use formulation comprising calcium citrate which can be easily taken by patients of any age and physical conditions, so as to ensure the recommended daily calcium intake, thus preventing and counteracting the onset of diseases related to bone mass loss, such as osteoporosis and fractures.

SUMMARY OF THE INVENTION

The inventors have surprisingly found that the objects of the present invention could be achieved by making a formulation in the form of an aqueous suspension comprising calcium citrate, xanthan gum, and lactic acid.

DETAILED DESCRIPTION OF THE INVENTION

The invention therefore relates to a formulation in the form of an aqueous suspension comprising calcium citrate, xanthan gum, and lactic acid.

For the purposes of the present invention, the term "calcium citrate" is intended to mean any salt form obtainable between calcium ions and citrate ions, even in hydrated form, as well as any amorphous or polymorphous form thereof.

Preferably said calcium citrate is calcium citrate tetrahydrate.

The formulation in the form of an aqueous suspension of the invention comprises calcium citrate in a concentration, expressed as calcium, in the range from 20 to 100 mg per 1 ml of suspension, preferably in the range from 40 to 70 mg per 1 ml of suspension, more preferably of about 50 mg per 1 ml of suspension.

Said formulation in the form of an aqueous suspension of the invention comprises xanthan gum in a percentage concentration (w/w) in the range from 0.3 to 5% (w/w), preferably from 0.4 to 2% (w/w), more preferably of about 0.45% (w/w) with respect to the weight of the final formulation.

Said formulation in the form of an aqueous suspension of the invention comprises lactic acid in a percentage concentration (w/w) in the range from 0.1 to 0.5% (w/w), preferably from 0.25 to 0.35% (w/w), more preferably of about 0.27% (w/w) with respect to the weight of the final formulation.

Preferably said lactic acid is lactic acid in the form of an aqueous solution which comprises 80% by weight of lactic acid.

As it will be apparent from the experimental part that follows, the inventors surprisingly discovered that by suspending calcium citrate salt in an aqueous solution in the presence of xanthan gum and lactic acid, a ready-to-use suspension, stable over time, was obtained.

The invention is surprising since many types of solubilizing agents, complexing agents, viscosizing agents, and cosolvents were tested, individually and as mixture thereof, in order to obtain stable calcium citrate suspensions, but in most cases, even where an initial suspension was obtained, the same quickly tended to settle, already within a few hours, or at most a few days, giving rise to insoluble "cakes".

The specific combination, instead, of xanthan gum, as a viscosizing agent, thickener and stabilizer, with calcium citrate in the presence of lactic acid, made surprisingly possible the preparation of stable suspensions, not subject to sedimentation, with pleasant organoleptic characteristics.

The aqueous suspension formulation of the invention can also be advantageously prepared as a unitary dose.

Said aqueous suspension of the invention in unitary dosage form comprises calcium citrate in an amount corresponding to a unitary dose of calcium in the range from 200 to 1500 mg, preferably from 400 to 1200 mg, still more preferably of 500 or 1000 mg.

Said aqueous suspension of the invention in unitary dosage form comprises xanthan gum in an amount in the range from 30 to 200 mg, preferably from 45 to 150 mg, still more preferably of about 50 or about 100 mg.

Said aqueous suspension of the invention in unitary dosage form comprises lactic acid, preferably lactic acid in the form of an aqueous solution comprising 80% by weight of lactic acid, in an amount in the range from 15 to 80 mg, preferably from 25 at 65 mg, still more preferably of about 30 or about 60 mg.

Said aqueous suspension of the invention in unitary dosage form has a total volume in the range from 5 to 30 ml, preferably from 8 to 25 ml, still more preferably of about 10 or about 20 ml.

The aqueous suspension formulation of the invention comprising calcium citrate, xanthan gum, and lactic acid, also in unitary dosage form, may further comprise any pharmaceutical excipient useful for the preparation thereof, such as for example sweeteners, solubilizers, pH modifiers, stabilizers, preservatives, flavoring agents.

Preferably the aqueous suspension of the invention comprises a sweetener, still more preferably said sweetener is sucralose.

Preferably the aqueous suspension of the invention comprises a preservative, still more preferably said preservative is potassium sorbate.

The aqueous suspension of the invention can also be easily flavored, in order to hide the typical "chalky" flavor of these preparations, so as to obtain a suspension that is more palatable and easier to take by patients, especially by pediatric patients.

Typical flavors that can be used are, for example, creme caramel flavor, orange flavor, cherry flavor, strawberry flavor, lemon flavor.

Preferably the aqueous suspension of the invention therefore also comprises a flavor, more preferably said flavor is cherry flavor.

In a preferred embodiment of the invention, the invention therefore concerns an aqueous suspension formulation comprising calcium citrate tetrahydrate, xanthan gum, lactic acid, preferably lactic acid in the form of an aqueous solution comprising 80% by weight of lactic acid, sucralose, potassium sorbate, and cherry flavor.

In particular, the aqueous suspension of the invention allows the administration of a unitary dose of 500 mg of calcium, by the intake of a reduced volume of preparation, generally in the range from 5 to 15 ml, preferably of about 10 ml, in the form of readily assimilable calcium citrate.

The possibility offered by the aqueous suspension of the present invention to provide a unitary dose of 500 mg of calcium by a single intake also allows, with only two intakes per day, to reach the daily calcium dosage recommended by the scientific and medical community.

In addition, the possibility offered by the aqueous suspension to provide the unitary dose of 500 mg of calcium in such a small volume, makes it easy and pleasant its intake even by subjects with swallowing difficulties.

The formulation in the form of an aqueous suspension of the invention can therefore be readily taken from elderly patients and from pediatric patients.

The formulation in the form of an aqueous suspension of the invention may therefore be effectively used in the calcium supplementation of subjects in need of supplementation, therefore, for example, in the prevention and treatment of diseases characterized by bone mass loss, such as osteoporosis, fractures, chronic diarrhea syndromes, hypertension, colon cancer.

Furthermore, the aqueous suspension of the invention, filled into flexible containers, such as for example cheer pack or stick pack, preferably stick pack, makes it possible for the patient the intake in any place or time of the day, since these containers are not bulky and are easily transportable, they can also be worn inside clothes, for example simply inside pockets.

The invention, therefore, also concerns a single-dose container, preferably flexible, still more preferably a stick pack, containing a pharmaceutical preparation or nutritional supplement in the form of an aqueous suspension comprising calcium citrate, xanthan gum, and lactic acid.

Preferably said calcium citrate is calcium citrate tetrahydrate.

Preferably said lactic acid is lactic acid in the form of an aqueous solution which comprises 80% by weight of lactic acid.

In a further embodiment of the invention, the invention therefore concerns a single-dose stick pack containing an aqueous suspension comprising calcium citrate, preferably calcium citrate tetrahydrate, xanthan gum, lactic acid, preferably in the form of an aqueous solution comprising 80% by weight of lactic acid, sucralose, potassium sorbate, and cherry flavor.

Preferably said single-dose stick pack contains about 10 ml of an aqueous suspension comprising calcium citrate tetrahydrate in an amount equivalent to a unitary dose of about 500 mg of calcium, xanthan gum, lactic acid, preferably 80% lactic acid, sucralose, potassium sorbate, and cherry flavor.

Still more preferably, said single-dose stick pack containing about 10 ml of the aqueous suspension of the invention, contains calcium citrate tetrahydrate in an amount equivalent to a unitary dose of about 500 mg of calcium, about 50 mg of xanthan gum, about 30 mg of 80% lactic acid, about 2 mg of sucralose, about 22 mg of potassium sorbate, and about 9 mg of cherry flavor.

As it will also be apparent from the experimental part that follows, the formulations in the form of an aqueous suspension of the invention, comprising xanthan gum in combination with calcium citrate, in the presence of lactic acid, proved to be particularly stable even when using high doses of calcium citrate and small suspension volumes. The formulations of the invention resulted therefore advantageous to be easily taken by any type of patient in need of calcium supplementation, in particular elderly patients and pediatric patients.

It is to be understood that all the aspects identified as preferred and advantageous for the aqueous suspension formulations comprising calcium citrate described above are to be considered likewise preferred and advantageous also for the single-dose containers containing said formulations, and respective uses thereof in the treatment of patients in need of calcium supplementation.

Examples of embodiments of the present invention are provided below as non-limiting examples.

EXPERIMENTAL PART

Example 1

With the aim of obtaining stable suspensions, various solutions were prepared by dispersing calcium citrate tetrahydrate in deionized water in the presence of various excipients having solubilizing, stabilizing, and viscosizing properties. In the following Table 1, some exemplary formulations among the dozens of tested formulations are reported, in particular A-H formulations obtained by mixing in deionized water the various ingredients in the weight proportions shown in the table are reported.

TABLE 1

| Ingredients | A % (w/w) | B % (w/w) | C % (w/w) | D % (w/w) | E % (w/w) | F % (w/w) | G % (w/w) | H % (w/w) |
|---|---|---|---|---|---|---|---|---|
| deionized water | 71.449 | 62.716 | 60.809 | 58.841 | 37.443 | 30.430 | 77.929 | 75.122 |
| calcium citrate tetrahydrate | 13.561 | 29.759 | 28.854 | 27.92 | 25.381 | 36.098 | 21.259 | 22.970 |
| tartaric acid | 13.561 | | | | | | | |
| malic acid | | | | 5.884 | 5.349 | | | |
| maleic acid | | | | 0.294 | | | | |
| citric acid | | | | | 10.698 | | | |
| 80% lactic acid | | | | | | 1.521 | 0.268 | 0.320 |
| sodium carboxymethylcellulose | 1.429 | | | | | | | |
| PEG200 | | | | | | 30.430 | | |
| PG alginate | | | | | | 1.521 | | |
| xanthan gum | | | | | | | 0.526 | 1.564 |
| sodium citrate | | 6.271 | 6.081 | 5.884 | 8.024 | | | |
| sodium gluconate | | | 3.040 | | 10.698 | | | |
| mannitol | | 1.254 | 1.216 | 1.177 | | | | |
| sorbitol | | | | | 1.337 | | | |
| sodium cyclamate | | | | | 1.070 | | | |
| sucralose | | | | | | | 0.018 | 0.024 |
| total | 100.000 | 100.000 | 100.000 | 100.000 | 100.000 | 100.000 | 100.000 | 100.000 |
| Suspension appearance | | | | | | | | |
| At time point t = 0 | fluid | fluid | fluid | fluid | fluid | fluid | fluid | fluid |
| At time point t = 24 hours | fluid | cake | very viscous | almost-cake | cake | very viscous | fluid | fluid |
| At time point t = 48 hours | very viscous | / | cake | cake | / | cake | fluid | fluid |

Once the various aqueous suspensions were prepared, their observation over time was carried out to verify their stability, and therefore the potential occurrence of sedimentation phenomena.

As reported in the same Table 1, in correspondence of each formulation, the appearance and the behavior of the suspension was recorded at the time of preparation (time point t=0), after 24 hours from preparation (time point t=24 hours), and finally after 48 hours from preparation (time point t=48 hours).

A-F suspensions proved to be completely unsatisfactory, due to more or less rapid sediment formation phenomena (cake) no longer re-suspendable.

Only G-H formulations, comprising both xanthan gum and lactic acid, in particular an aqueous solution comprising 80% by weight of lactic acid, as stabilizing, viscosizing, suspending and/or solubilizing agents, allowed to obtain suspensions that remained fluid even after 48 hours from preparation thereof.

Example 2

In light of the excellent results obtained in the case of G and H formulations of Example 1, a bulk of about 11 kg of suspension I, obtained by mixing the ingredients listed in the following Table 2 in the specified proportions by weight, was prepared.

TABLE 2

| | I | |
|---|---|---|
| | kg | % (w/w) |
| Ingredients | | |
| Deionized water | 8.675 | 77.726 |
| calcium citrate tetrahydrate | 2.373 | 21.261 |
| 80% lactic acid | 0.030 | 0.269 |
| xanthan gum | 0.050 | 0.448 |
| potassium sorbate | 0.022 | 0.197 |

TABLE 2-continued

| | I | |
|---|---|---|
| | kg | % (w/w) |
| sucralose | 0.002 | 0.018 |
| cherry flavor | 0.009 | 0.081 |
| total | 11.161 | 100.000 |
| Suspension appearance | | |
| At time point t = 0 | fluid | fluid |
| At time point t = 24 hours | fluid | fluid |
| At time point t = 48 hours | fluid | fluid |

In particular, the indicated amounts of sucralose and potassium sorbate were initially dissolved in water in an appropriate mixer; to said solution, calcium citrate tetrahydrate was then added under vigorous stirring, after which xanthan gum was added portionwise, still under stirring. At the end, the suspension was acidified with lactic acid, and then the preparation was completed by cherry flavor addition. The suspension thus obtained was perfectly stable, even after several days from preparation, with excellent organoleptic characteristics, and suitable also for pediatric administration.

Example 3

The bulk of calcium citrate aqueous suspension formulation I of Example 2 was used to prepare single-dose stick pack containers.

The suspension was then dosed, using stick filling machines, into the target flexible stick pack containers, so as to fill about 10 ml of suspension into each single-dose container.

Each single-dose container thus made contained therefore about 10 ml of calcium citrate tetrahydrate aqueous suspension, corresponding to a unitary dose of about 500 mg of calcium, about 50 mg of xanthan gum, about 30 mg of 80% lactic acid (i.e. in the form of an aqueous solution comprising 80% by weight of lactic acid), about 2 mg of sucralose, about 22 mg of potassium sorbate, and about 9 mg of cherry flavor.

Example 4

The stability of the aqueous suspension formulations I of Example 2, packed in the stick pack format of Example 3, was tested, subjecting a representative number of said stick packs to stability tests, specifically under the following conditions:
(a) long term: temperature of about 25° C. and relative humidity of about 60%;
(b) intermediate: temperature of about 30° C. and relative humidity of about 65%;
(c) accelerated: temperature of about 40° C. and relative humidity of about 75%.

Therefore, constant analytical checks were carried out in order to verify the stability of the samples over time, in particular pH and calcium assay values were determined, before the start of stability and after 1, 3, and 6 months of conditioning in the above specified temperature and humidity conditions.

The pH value, initially equal to about 4.4, remained for the entire observation period always within the range allowed by the specifications, i.e. always within the range comprised between 4.3 and 4.5, in all tested stability conditions (a), (b) and (c).

The calcium assay, initially equal to about 500 mg per stick pack, never exceeded the permitted variation specifications during the entire observation period.

The suspension I contained in the stick packs thus remained absolutely stable even after 6 months from the preparation thereof, even when placed under particularly stressful conditions, such as conditions (b) and (c).

The stick pack therefore proved to be a safe format, easy to produce and to market, suitable to ensure a high compliance of patients in need of calcium supplementation, thanks to its lightness and ease of transport, simplicity of openness, immediacy of intake at any time of the day, rapidity of intake thanks to the reduced volumes, practicalness of intake not requiring additional dispersing means, such as in the case of granules or powders currently on the market, as well as pleasing intake, thanks to the presence of flavors; characteristics that as a whole made the product thus formulated a highly acceptable supplement for all types of patients, especially the most difficult ones, such as the elderly and pediatric patients.

As it is apparent, therefore, the formulations in the form of an aqueous suspension of the invention, comprising xanthan gum in combination with calcium citrate, in the presence of lactic acid, preferably of an aqueous solution comprising 80% by weight of lactic acid, proved to be surprisingly stable, also using high doses of calcium citrate and small volumes of suspension, even after very long observation times and under particularly stressing storage conditions, thus representing an ideal solution for the administration of calcium in a readily bioavailable form, such as calcium citrate, to patients who are in need of supplementation thereof to prevent or counteract diseases related to bone mass loss, such as osteoporosis and fractures.

The invention claimed is:

1. A formulation in the form of an aqueous suspension comprising calcium citrate, xanthan gum, and lactic acid, wherein calcium citrate is in a concentration, expressed with reference to calcium, in the range from 25 to 100 mg per 1 ml of suspension,
    wherein xanthan gum is in a percentage concentration (w/w) in the range from 0.3 to 5% (w/w) with respect to the total weight of the formulation, and
    wherein lactic acid is in a percentage concentration (w/w) in the range from 0.1 to 0.5% (w/w) with respect to the total weight of the formulation.

2. The formulation in the form of an aqueous suspension according to claim 1, wherein calcium citrate is calcium citrate tetrahydrate.

3. The formulation in the form of an aqueous suspension according to claim 1, wherein lactic acid is 80% lactic acid.

4. The formulation in the form of an aqueous suspension according to claim 1, wherein calcium citrate is in a concentration, expressed with reference to calcium of about 50 mg per 1 ml of suspension.

5. The formulation in the form of an aqueous suspension according to claim 1, further comprising sucralose.

6. The formulation in the form of an aqueous suspension according to claim 1, wherein lactic acid is in the form of an aqueous solution comprising 80% by weight of lactic acid.

7. The formulation in the form of an aqueous suspension according to claim 6, wherein lactic acid is in a percentage concentration (w/w) in the range from 0.25 to 0.35% (w/w) with respect to the total weight of the formulation.

8. The formulation in the form of an aqueous suspension according to claim 7, wherein lactic acid is in a percentage concentration (w/w) of about 0.27% (w/w) with respect to the total weight of the formulation.

9. The formulation in the form of an aqueous suspension according to claim 7, wherein lactic acid is in the form of an aqueous solution comprising 80% by weight of lactic acid.

10. The formulation in the form of an aqueous suspension according to claim 1, wherein the aqueous suspension is in the form of a unitary dose.

11. The formulation in the form of an aqueous suspension according to claim 10, wherein the aqueous suspension in the form of a unitary dose comprises calcium citrate in an amount corresponding to a unitary dose of calcium in the range from 200 to 1500 mg.

12. The formulation in the form of an aqueous suspension according to claim 11, wherein the aqueous suspension in the form of a unitary dose comprises calcium citrate in an amount corresponding to a unitary dose of calcium of about 500 mg or about 1000 mg.

13. The formulation in the form of an aqueous suspension according to claim 11, wherein the aqueous suspension in the form of a unitary dose comprises calcium citrate in an amount corresponding to a unitary dose of calcium in the range from 400 to 1200 mg.

14. The formulation in the form of an aqueous suspension according to claim 10, wherein the xanthan gum is in an amount by weight in the range from 30 to 200 mg.

15. The formulation in the form of an aqueous suspension according to claim 14, wherein the xanthan gum is in an amount by weight in the range from 45 to 150 mg.

16. The formulation in the form of an aqueous suspension according to claim 15, wherein the xanthan gum is in an amount by weight of about 50 or about 100 mg.

17. The formulation in the form of an aqueous suspension according to claim 10, wherein lactic acid, is in an amount in the range from 15 to 80 mg.

18. The formulation in the form of an aqueous suspension according to claim 17, wherein lactic acid, is in an amount in the range from 25 to 65 mg.

19. The formulation in the form of an aqueous suspension according to claim 18, wherein lactic acid is in an amount of about 30 or about 60 mg.

20. The formulation in the form of an aqueous suspension according to claim 17, wherein lactic acid is in the form of an aqueous solution comprising 80% by weight of lactic acid.

21. The formulation in the form of an aqueous suspension according to claim 10, wherein the total volume of said aqueous suspension is in the range from 5 to 30 ml.

22. The formulation in the form of an aqueous suspension according to claim 21, wherein the total volume of said aqueous suspension is in the range from 8 to 25 ml.

23. The formulation in the form of an aqueous suspension according to claim 22, wherein the total volume of said aqueous suspension is of about 10 or about 20 ml.

24. The formulation in the form of an aqueous suspension according to claim 10 comprising calcium citrate in an amount corresponding to a unitary dose of calcium of 500 mg in a total volume of about 10 ml.

25. A single-dose flexible container containing a unitary dose of a pharmaceutical preparation or a nutritional supplement comprising the formulation according to claim 1.

26. The container according to claim 25, wherein the flexible container is a cheer pack or a stick pack.

27. The container according to claim 25, said formulation containing about 10 ml of an aqueous suspension comprising calcium citrate tetrahydrate in an amount equivalent to a unitary dose of about 500 mg of calcium, about 50 mg of xanthan gum, about 30 mg of lactic acid in the form of a compound comprising 80% by weight of lactic acid.

28. The container according to claim 27, said formulation further containing sucralose.

29. The formulation in the form of an aqueous suspension according to claim 1, wherein xanthan gum is in a percentage concentration (w/w) in the range from 0.4 to 2% (w/w) with respect to the total weight of the formulation.

30. The formulation in the form of an aqueous suspension according to claim 29, wherein xanthan gum is in a percentage concentration (w/w) of about 0.45% (w/w) with respect to the total weight of the formulation.

31. A method of treating a subject in need of calcium supplementation comprising administering to said subject in need the formulation in the form of an aqueous suspension according to claim 1.

32. The method according to claim 31, wherein the subject in need of calcium supplementation is an elderly patient or a pediatric patient.

33. The method according to claim 31, wherein the subject in need of calcium supplementation is a patient affected by diseases related to bone mass loss, said disease being selected from the group consisting of osteoporosis, fractures, chronic diarrhea syndromes, hypertension and colon cancer.

* * * * *